United States Patent [19]
Cobb et al.

[11] Patent Number: 5,488,124
[45] Date of Patent: Jan. 30, 1996

[54] ALKYLPOLYETHER SILOXANES

[75] Inventors: Vicky S. Cobb, Elsie; Beth I. Gutek, Freeland; Gary E. Le Grow, Midland, all of Mich.

[73] Assignee: Dow Corning Corporation, Midland, Mich.

[21] Appl. No.: 387,515

[22] Filed: Feb. 13, 1995

[51] Int. Cl.$^6$ .................................................. C07F 7/08
[52] U.S. Cl. ................ 556/445; 424/78.02; 424/78.08
[58] Field of Search ...................... 556/445; 514/844, 514/847, 873, 63; 424/78.03, 78.02

[56]  References Cited

U.S. PATENT DOCUMENTS

| | | | |
|---|---|---|---|
| 4,988,504 | 1/1991 | Zotto et al. | 556/445 X |
| 5,104,998 | 4/1992 | Ichinohe | 556/445 |
| 5,306,737 | 4/1994 | Burkhart et al. | 556/455 X |

*Primary Examiner*—Paul F. Shaver
*Attorney, Agent, or Firm*—James De Cesare

[57]  ABSTRACT

New alkylpolyether siloxanes are prepared by reacting an unsaturated ether with alkylhydrido siloxanes such as (i) comonomers $RSi(OSiMe_2H)_3$, (ii) oligomers $(HMe_2SiO)_2$—$Si(R)$—$O$—$Si(R)$—$(OSiMe_2H)_2$, and (iii) higher molecular weight siloxane species $RSi[(OSiMe_2)_xOSiMe_2H]_3$ and $[HMe_2SiO(Me_2SiO)_x]_2Si(R)O(R)Si[(OSiMe_2)_xOSiMe_2H]_2$. R is a $C_2$ to $C_{18}$ straight-chain or branched-chain alkyl substituent.

17 Claims, No Drawings

ALKYLPOLYETHER SILOXANES

BACKGROUND OF THE INVENTION

In copending U.S. application Ser. No. 08/338,940, filed Nov. 14, 1994, now U.S. Pat. No. 5,446,185 and assigned to the assignee of this invention, there is described a family of new alkylhydrido siloxanes including comonomers of the formula $RSi(OSiMe_2H)_3$, oligomers of the formula $(HMe_2SiO)_2$—$Si(R)$—$O$—$Si(R)$—$(OSiMe_2H)_2$, and higher molecular weight siloxanes of the formula $RSi[(OSiMe_2)_xOSiMe_2H]_3$ and $[HMe_2SiO(Me_2SiO)_x]_2Si(R)O(R)Si[(OSiMe_2)_xOSiMe_2H]_2$; in which Me is methyl; R is a $C_2$ to $C_{18}$ straight-chain or branched-chain alkyl substituent; and x has a value of 1–200.

This invention is an improvement on the prior application in which a new family of alkylpolyether siloxanes are provided by hydrosilylation of the alkylhydrido siloxanes in the prior application. These alkylpolyether siloxanes are useful as conditioning agents in personal care compositions applied to human skin.

SUMMARY OF THE INVENTION

The invention is directed to new alkylpolyether siloxanes. The siloxanes are compounds covered by one of the formulas: $RSi(OSiMe_2Q)_3$, $(QMe_2SiO)_2$—$Si(R)$—$O$—$Si(R)$—$(OSiMe_2Q)_2$, $RSi[(OSiMe_2)_xOSiMe_2Q]_3$ and $[QMe_2SiO(Me_2SiO)_x]_2Si(R)O(R)Si[(OSiMe_2)_xOSiMe_2Q]_2$. In the formulas, Me is methyl; R is a $C_2$ to $C_{18}$ straight-chain or branched-chain alkyl substituent; x has a value of 1–200; and Q is a radical containing oxyethylene groups, oxypropylene groups, oxybutylene groups, or any combination of oxyethylene groups, oxypropylene groups, or oxybutylene groups. A representative Q radical is —$(CH_2)_y(OCH_2CH_2)_a(OCH_2CHCH_3)_b[OCH_2CH(CH_2CH_3)]_c$ OR'. In the Q radical, R' can be hydrogen; an alkyl radical such as methyl, ethyl, propyl, or butyl; an aryl radical such as phenyl; an aralkyl radical such as benzyl; or an acyl radical such as acetyl. The integer y is 3–6; a is 0–120; b is 0–50; and c is 0–50; with the proviso that a, b, and c, cannot all be zero. In addition, Q can be the same or different.

Where Q is different, the compounds covered by the formula $RSi(OSiMe_2Q)_3$ can be more conveniently expressed as $RSi[(OSiMe_2Q)_z(OSiMe_2Q')_{3-z}]$ in which z is 1 or 2. Similarly, the compounds covered by the formula $RSi[(OSiMe_2)_xOSiMe_2Q]_3$ can be more conveniently expressed as $RSi[(OSiMe_2)_x(OSiMe_2Q)]_z[(OSiMe_2)_x(OSiMe_2Q')]_{3-z}$ in which z is 1 or 2.

It is therefore an object of the present invention to provide a novel family of alkylpolyether siloxanes as new compositions of matter.

These and other objects of the present invention will become more apparent from a consideration of the following detailed description thereof.

DETAILED DESCRIPTION OF THE INVENTION

Siloxanes according to the invention can be prepared by hydrosilylation of alkylhydrido siloxanes with alkenyl ether terminated organic oxyalkylene compounds. Alkylhydrido siloxanes such as $RSi(OSiMe_2H)_3$ and $(HMe_2SiO)_2$—$Si(R)$—$O$—$Si(R)$—$(OSiMe_2H)_2$ can be prepared in high yield by hydrolysis of the corresponding chlorosilanes. Details of the hydrolysis reaction are described in the copending application Ser. No. 08/338,940, filed Nov. 14, 1994.

The reaction is briefly depicted in "Scheme 1".

Scheme 1

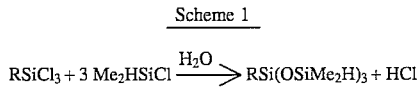

According to "Scheme 1", the amount of $RSi(OSiMe_2H)_3$ obtained in the hydrolysis is dependent upon the temperature at which the reaction is conducted. Where R is n-propyl (Pt), and when the temperature is maintained slightly below 15° C., 83% of the product is $RSi(OSiMe_2H)_3$. At 30° C., 79% of the product is $RSi(OSiMe_2H)_3$; while at 40° C., 47% of the product is $RSi(OSiMe_2H)_3$. At higher temperatures, larger amounts of $(HMe_2SiO)_2$—$Si(R)$—$O$—$Si(R)$—$(OSiMe_2H)_2$ and higher molecular weight siloxane species are formed.

The products $RSi(OSiMe_2H)_3$ and $(HMe_2SiO)_2Si(R)O(R)Si(OSiMe_2H)_2$ from the hydrolysis in "Scheme 1", can be used in the preparation of the higher molecular weight siloxane species. The higher molecular weight materials are prepared by an acid catalyzed ring opening of cyclic siloxanes such as a dimethylcyclosiloxane, followed by insertion into $RSi(OSiMe_2H)_3$ and $(HMe_2SiO)_2Si(R)O(R)Si(OSiMe_2H)_2$. Such a process is also described in detail in the copending application Ser. No. 08/338,940, filed Nov. 14, 1994, and is briefly depicted below in "Scheme 2".

Scheme 2

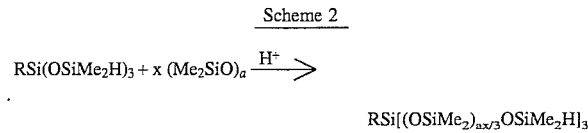

The acid catalyst in "Scheme 2" can be hydrochloric acid, sulfuric acid, phosphoric acid, oxalic acid, acetic acid, trichloroacetic acid, or trifluoromethane sulfonic acid. The method in "Scheme 2" is carried out by creating a mixture of the cyclic siloxane $(Me_2SiO)_a$, $RSi(OSiMe_2H)_3$ or $(HMe_2SiO)_2Si(R)O(R)Si(OSiMe_2H)_2$, and the acid catalyst. The mixture is heated with agitation at a polymerization reaction temperature, until essentially all of the cyclic siloxane is reacted. The time required will vary depending on the reactants and the reaction conditions. The polymerization reaction in "Scheme 2" is stopped at the desired level of conversion of cyclic siloxane, by using methods known in the art such as neutralization of the catalyst by the addition of an equal, or slightly greater stoichiometric amount of base. A weak base may be used to neutralize the reaction.

The siloxanes depicted in "Scheme 1" and "Scheme 2" include comonomers, oligomers, and higher molecular weight siloxane species, and are used as intermediates in the preparation of the alkylpolyether siloxanes of the invention. The R group in "Scheme 1" and "Scheme 2" is a $C_2$ to $C_{18}$ straight-chain (unbranched) or branched-chain alkyl substituent. Suitable R substituents are ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

The cyclic siloxanes most suitable for "Scheme 2" are (i) hexamethylcyclotrisiloxane with a boiling point of 133° C.

and the formula [(Me$_2$)SiO]$_3$; (ii) octamethylcyclotetrasiloxane with a boiling point of 171° C. and the formula [(Me$_2$)SiO]$_4$; (iii) decamethylcyclopentasiloxane with a boiling point of 205° C. and the formula [(Me$_2$)SiO]$_5$; and (iv) dodecamethylcyclohexasiloxane with a boiling point of 245° C. and the formula [(Me$_2$)SiO]$_6$.

In the process of preparing the alkylpolyether siloxanes of the invention, one or more unsaturated ethers are reacted with one of the above described alkylhydrido siloxanes containing the ≡SiH group. Suitable alkenyl ether terminated organic oxyalkylene compounds which can be employed contain at least three to about ten carbon atoms in the alkenyl group, and examples of groups which can be used are allyl, isopropenyl, 2-butenyl, 3-butenyl, or hexenyl. Allyl is the most preferred alkenyl group, and representative allyl ether terminated organic oxyalkylene compounds are: H$_2$C=CH—CH$_2$—O—(CH$_2$—CH$_2$O)$_m$—R"; H$_2$C=CH—CH$_2$—O—[CH$_2$—CH (CH$_3$)O]$_n$—R"; and H$_2$C=CH—CH$_2$—O—(CH$_2$—CH$_2$O)$_m$—[CH$_2$—CH(CH$_3$)O]$_n$—R".

In those formulas, m is 1–120; n is 1–50; and R" is hydrogen; an alkyl radical such as methyl, ethyl, propyl, or butyl; an aryl radical such as phenyl; an aralkyl radical such as benzyl; or an acyl radical such as acetyl.

It is preferred to conduct the hydrosilylation reaction with an allyl to ≡SiH ratio of 1.0 to 1.2, although other ratios can be employed. The alkylpolyether siloxane products of the hydrosilylation reaction are best made by reacting the allyl ether of the desired oxyalkylene compound with the corresponding siloxane containing ≡SiH groups. This reaction is best carried out by heating a mixture of the reactants in the presence of a platinum catalyst, such as platinum dispersed on an inert carrier or a compound of platinum such as chloroplatinic acid, at temperatures from 30°–100° C.

Representative hydrosilylation reactions according to the invention are depicted in Schemes 3 and 4 as follows:

Scheme 3

RSi(OSiMe$_2$H)$_3$ +

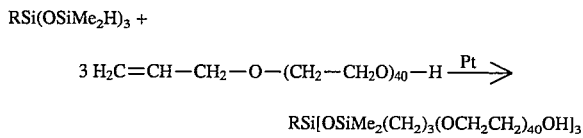

RSi[OSiMe$_2$(CH$_2$)$_3$(OCH$_2$CH$_2$)$_{40}$OH]$_3$

Scheme 4

[HMe$_2$SiO(Me$_2$SiO)$_x$]$_2$Si(R)O(R)Si[(OSiMe$_2$)$_x$OSiMe$_2$H]$_2$ +

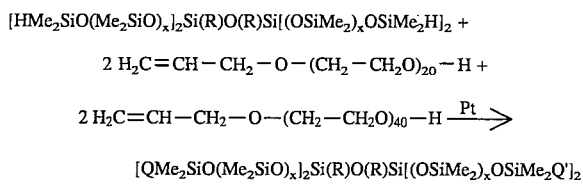

[QMe$_2$SiO(Me$_2$SiO)$_x$]$_2$Si(R)O(R)Si[(OSiMe$_2$)$_x$OSiMe$_2$Q']$_2$

In Scheme 4, Q is —(CH$_2$)$_3$(OCH$_2$CH$_2$)$_{20}$OH; Q' is —(CH$_2$)$_3$(OCH$_2$CH$_2$)$_{40}$OH; and the two groups Q and Q' are randomly arranged on the siloxane in a ratio of about 50:50.

Hydrosilylation catalysts are well known in the art and the interested reader is referred to the following patents for detailed descriptions regarding their preparation and use: Speier, U.S. Pat. No. 2,823,218; Willing, U.S. Pat. No. 3,419,359; Kookootsedes, U.S. Pat. No. 3,445,420; Polmanteer et al, U.S. Pat. No. 3,697,473; Nitzsche, U.S. Pat. No. 3,814,731; Chandra, U.S. Pat. No. 3,890,359; and Sandford, U.S. Pat. No. 4,123,604. Many of the catalysts known in the art require the reactants to be heated in order for reaction to occur. When such catalysts are employed, this requirement must be taken into consideration.

The concentration of the catalyst may be determined by routine experimentation. Typically, however, the effective amount of catalyst should be in a range so as to provide from about 1–1,000 parts per million (ppm) of platinum by weight in the compositions of the present invention.

This invention is illustrated in more detail in the following examples.

EXAMPLE I

Preparation of PrSi(OSiMe$_2$H)$_3$ n-propyltris (dimethylsiloxy) silane

A mixture of PrSiCl$_3$ (59.92 g, 0.338 moles) and Me$_2$HSiCl (95.90 g, 1.014 moles) was added drop-wise to a 3-necked round bottom flask containing ice water (166.0 g, 9.22 moles). The flask was fitted with a thermometer, a mechanical stirrer, and a pressure equalizing addition funnel. The chlorosilanes were added drop-wise through the addition funnel at a rate to maintain a temperature in the flask slightly below 15° C. The solution was vigorously mixed throughout this addition. The solution was stirred for 30 minutes after completion of the chlorosilane addition. An aqueous layer was drawn off, followed by several NaHCO$_3$ washes, and several water washes until neutral to pH paper. The siloxane was dried over MgSO$_4$ overnight and filtered under N$_2$ pressure, yielding a clear, colorless liquid. The final product contained 83% of PrSi(OSiMe$_2$H)$_3$; 9% of (HMe$_2$SiO)$_2$Si(Pr)OSi(Pr)(OSiMe$_2$H)$_2$, and 8% of other siloxane impurities. Characterization included Si-29 Nuclear Magnetic Resonance (NMR), Gas Chromatography/Mass Spectrometry (GC/MS), and Gas Chromatography/Flame Ionization Detection (GC/FID).

EXAMPLE II

Example I was repeated, except that room temperature water was used instead of ice water, and the temperature was allowed to rise to 30° C. The final product contained 79% of PrSi(OSiMe$_2$H)$_3$, 12% of (HMe$_2$SiO)$_2$Si(Pr)OSi(Pr)(OSiMe$_2$H)$_2$, and 9% of other siloxane impurities.

EXAMPLE III

Example I was again repeated, except that room temperature water was used instead of ice water, and the temperature was allowed to rise to 40° C. The final product contained 47% of PrSi(OSiMe$_2$H)$_3$, 30% of (HMe$_2$SiO)$_2$Si(Pr)OSi(Pr)(OSiMe$_2$H)$_2$, and 23% of other siloxane impurities.

EXAMPLE IV

Preparation of PrSi[(OSiMe$_2$)$_{3.5}$OSiMe$_2$H]$_3$

A solution of n-propyltris(dimethylsiloxy) silane PrSi(OSiMe$_2$H)$_3$ (18.94 g, 0.064 moles) prepared in Example I, (Me$_2$SiO)$_4$ cyclosiloxane (49.82 g, 0.672 moles), and 41 microliters of trifluoromethane sulfonic acid, was heated to 70° C. The flask was fitted with a water cooled condensing column, a magnetic stirrer, and a thermometer. The flask was flushed with N$_2$ prior to heating, followed by N$_2$ positive pressure through the top of the condenser. After heating the flask at 70° C. for four hours, the solution was cooled to room temperature, followed by the addition of NaHCO$_3$ (1.0 g) and diatomaceous earth (Celite) (1.0 g). The mixture was stirred for 4 hours, followed by filtration under N$_2$ pressure, and yielded a clear, colorless liquid. The final average structure determined by Si-29 NMR was $(PrSi)_{1.0}[(OSiMe_2)_{3.5}OSiMe_2H]_3$. In that structure, the value "1.0" was plus or minus 0.2; the value "3.5" was plus or minus 0.5; and the value "3.0" was plus or minus 0.2. Dimethyl cyclic siloxanes were also present in the product.

EXAMPLE V

Preparation of $PrSi(OSiMe_2Q)_3$ where Q is
—$CH_2CH_2CH_2O(CH_2CH_2O)_{20}H$

Allyloxy initiated ethylene oxide homopolymer (208.51 g, 0.218 moles) of the formula $H_2C=CH-CH_2-O-(CH_2CH_2O)_{20}H$ and isopropyl alcohol (60.0 g) were weighed into a three necked round bottom flask equipped with a thermometer, mechanical stirrer, and a Claisen adapter fitted with a water cooled condenser and a pressure equalizing addition funnel. Homogeneous platinum catalyst (10 ppm as Pt) was added to the 40° C. solution. Dropwise addition of $PrSi(OSiMe_2H)_3$ (18.69 g, 0.0631 moles) was adjusted to maintain the temperature near 65° C. throughout the addition. The temperature was increased to 90° C. until no SiH was observed in the InfraRed spectrum. Removal of isopropyl alcohol under reduced pressure yielded the product, a waxy solid at room temperature.

EXAMPLE VI

Preparation of $PrSi(OSiMe_2Q)_3$ where Q is
—$CH_2CH_2CH_2O(CH_2CH_2O)_{40}H$

Allyloxy initiated ethylene oxide homopolymer (187.84 g, 0.136 moles) of the formula $H_2C=CH-CH_2-O-(CH_2CH_2O)_{40}H$, $PrSi(OSiMe_2H)_3$ (12.16 g, 0.0411 moles), and isopropyl alcohol (40.0 g) were weighed into a three necked round bottom flask equipped with a thermometer, mechanical stirrer, and a water cooled condenser. Homogeneous platinum catalyst (9.2 ppm as Pt) was added to the 80° C. solution. The temperature was maintained at 90° C. until the SiH level was below 5 ppm. Removal of isopropyl alcohol under reduced pressure yielded the product, a waxy solid at room temperature.

EXAMPLE VII

Preparation of $PrSi[(OSiMe_2Q)_{3-x}(OSiMe_2Q')_x]$
where x=0–3, Q is —$CH_2CH_2CH_2O(CH_2CH_2O)_7H$,
and Q' is
—$CH_2CH_2CH_2O(CH_2CH_2O)_{18}(CH_2CHCH_3O)_{18}H$ Allyloxy initiated ethylene oxide homopolymer (26.72 g, 0.073 moles) of the formula $H_2C=CH-CH_2-O-(CH_2CH_2O)_7H$, allyloxy initiated ethylene oxide/propylene oxide copolymer (69.14 g, 0.0365 moles) of the formula $H_2C=CH-CH_2-O-(CH_2CH_2O)_{18}(CH_2CHCH_3O)_{18}H$, $PrSi(OSiMe_2H)_3$ (10.13 g, 0.0342 moles), and isopropyl alcohol (26.0 g) were weighed into a three necked round bottom flask equipped with a thermometer, mechanical stirrer, and a water cooled condenser. Homogeneous platinum catalyst (10 ppm as Pt) was added to the 75° C. solution. The temperature was maintained at 90° C. until the SiH level was below 5 ppm. Removal of isopropyl alcohol under reduced pressure yielded the product, a straw colored liquid.

Other variations may be made in the compounds described without departing from the concept of the invention. The forms of invention described are only exemplary and not intended as limitations on the scope of invention defined in the claims.

That which is claimed is:

1. Compounds selected from the group consisting of $RSi(OSiMe_2Q)_3$ and $(QMe_2SiO)_2-Si(R)-O-Si(R)-(OSiMe_2Q)_2$, wherein Me is methyl; R is a $C_2$ to $C_{18}$ straight-chain or branched-chain alkyl substituent; and Q is a radical containing oxyethylene groups, oxypropylene groups, oxybutylene groups, or combinations of oxyethylene groups, oxypropylene groups, and oxybutylene groups.

2. Compounds according to claim 1 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

3. Compounds according to claim 2 in which the Q radical is —$(CH_2)_y(OCH_2CH_2)_a(OCH_2CHCH_3)_b$ $[OCH_2CH(CH_2CH_3)]_c$ OR' wherein R' is hydrogen, an alkyl radical, an aryl radical, an aralkyl radical, or an acyl radical; y is 3–6; a is 0–120; b is 0–50; and c is 0–50; with the proviso that a, b, and c, cannot all be zero.

4. Compounds according to claim 3 in which R is n-propyl.

5. A method of conditioning skin comprising applying to the skin a skin conditioning effective amount of a compound as defined in claim 1.

6. Siloxane compounds selected from the group consisting of $RSi[(OSiMe_2Q)_z(OSiMe_2Q')_{3-z}]$ and $(QMe_2SiO)_2-Si(R)-O-Si(R)-(OSiMe_2 Q')_2$, wherein Me is methyl; R is a $C_2$ to $C_{18}$ straight-chain or branched-chain alkyl substituent; z is 1 or 2; Q and Q' are the same or different radicals containing oxyethylene groups, oxypropylene groups, oxybutylene groups, or combinations of oxyethylene groups, oxypropylene groups, and oxybutylene groups; and Q and Q' are randomly arranged on the siloxane.

7. Compounds according to claim 6 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

8. Compounds according to claim 7 in which the Q and Q' radicals are —$(CH_2)_y(OCH_2CH_2)_a(OCH_2CHCH_3)_b$ $[OCH_2CH(CH_2 CH_3)]_cOR'$ wherein R' is hydrogen, an alkyl radical, an aryl radical, an aralkyl radical, or an acyl radical; y is 3–6; a is 0–120; b is 0–50; and c is 0–50; with the proviso that a, b, and c, cannot all be zero.

9. Compounds according to claim 8 in which Q and Q' are randomly arranged on the siloxane in a ratio of about 50:50.

10. Compounds according to claim 9 in which R is n-propyl.

11. A method of conditioning skin comprising applying to the skin a skin conditioning effective amount of a compound as defined in claim 6.

12. Compounds selected from the group consisting of $RSi[(OSiMe_2)_xOSiMe_2Q]_3$ and $[QMe_2SiO(Me_2SiO)_x]_2Si(R)O(R)Si[(OSiMe_2)_xOSiMe_2Q]_2$ wherein Me is methyl; R is a $C_2$ to $C_{18}$ straight-chain or branched-chain alkyl substituent; x has a value of 1–200; and Q consists only of an oxyethylene group or an oxybutylene group.

13. Compounds according to claim 12 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

14. A method of conditioning skin comprising applying to the skin a skin conditioning effective amount of a compound as defined in claim 12.

15. Siloxane compounds selected from the group consisting of $RSi[(OSiMe_2)_x(OSiMe_2Q)]_z[(OSiMe_2)_x(OSiMe_2Q')]_{3-z}$ and $[QMe_2SiO(Me_2SiO)_x]_2Si(R)O(R)Si[(OSiMe_2)_xOSiMe_2Q']_2$ wherein Me is methyl; R is a $C_2$ to $C_{18}$ straight-chain or branched-chain alkyl substituent; x has a value of 1–200; z is 1 or 2; Q consists only of an oxyethylene group or an oxybutylene group; Q' is the same or a different radical containing oxyethylene groups, oxypropylene groups, oxybutylene groups, or combinations of oxyethylene groups, oxypropylene groups, and oxybutylene groups; Q and Q' being randomly arranged on the siloxane.

16. Compounds according to claim 15 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

17. A method of conditioning skin comprising applying to the skin a skin conditioning effective amount of a compound as defined in claim 15.

* * * * *